United States Patent [19]

Zaiger

[11] Plant 4,394

[45] Mar. 13, 1979

[54] PLUM TREE

[76] Inventor: Chris F. Zaiger, 537 Rosemore Ave., Modesto, Calif. 95351

[21] Appl. No.: 839,108

[22] Filed: Oct. 3, 1977

[51] Int. Cl.[2] ..... A01H 5/03
[52] U.S. Cl. ..... Plt./38
[58] Field of Search ..... Plt./38

*Primary Examiner*—Robert E. Bagwill
*Assistant Examiner*—James R. Feyrer

[57] ABSTRACT

This variety relates to a plum tree which is of medium to large size, medium dense, vigorous and upright in growth; and is a productive and regular bearer of medium to large, early ripening, firm yellow flesh, clingstone fruit having a red (9-C-8 to 10-D-8) skin color.

3 Drawing Figures

ORIGIN OF THE VARIETY

The present variety of plum tree was discovered by me as a bud sport of a Red Beaut (U.S. Plant Pat. No. 2,539) plum tree in my experimental orchard located in Modesto, Stanislaus County, Calif. A large number of budsticks were irradiated with Cobalt 60 at University of California, Davis, which were budded by me on new growth of established trees. Several mutations were discovered and repropagated for further testing and evaluation. One of which is the variety recognized by me as to the novel characteristics—which will hereinafter appear—of said bud sport, I propagated the variety in anticipation of ultimate introduction to the trade and to meet an existing demand for a plum so characterized.

ASEXUAL REPRODUCTION OF THE VARIETY

Asexual reproduction of the new variety by budding was performed by me at Modesto, Calif. and in maturity, such reproductions ran true to the original bud sport.

SUMMARY OF THE VARIETY

The present variety of plum tree is of medium to large size, vigorous, medium dense, upright in growth, and a productive and regular bearer of medium to large size, early ripening, clingstone fruit having firm, yellow flesh and a red skin color.

The present variety of plum tree is further characterized by:

1. Production of more fruiting spurs than the variety Red Beaut at an earlier age, usually produces fruit spurs the second year.
2. Production of larger fruit than Red Beaut.
3. The fruit being clingstone.
4. The flesh color of the fruit being yellow when full ripe.
5. The new variety blooms two to three days before Red Beaut.
6. The new variety matures two to three days before Red Beaut.

The foregoing characteristics definitely differentiate my new variety from the variety "Red Beaut", as well as from all other varieties of which I am aware.

DESCRIPTION OF THE DRAWING

The drawing is an illustration by photographic reproduction in color, of a branch with fruiting spurs, upper and lower surface of leaves and typical specimens of the fruit, one of the said fruit specimens being depicted in cross section with stone remaining in place.

DESCRIPTION OF THE VARIETY

The botanical details of this new and distinct variety of plum tree—with color definitions (except those in common color terms) referenced to Reinhold Color Atlas by A. Kornerup and J. H. Wanscher—are as follows:

Tree:
- *Size.*—Medium to large.
- *Vigor.*—Vigorous.
- *Growth.*—Upright.
- *Density.*—Medium dense.
- *Shape.*—Vase form.
- *Production.*—Productive.
- *Bearing.*—Regular bearer.

Trunk:
- *Form.*—Medium.
- *Texture.*—Shaggy.

Branches:
- *Size.*—Medium.
- *Texture.*—Medium rough.
- *Color.*—Grayish brown to reddish brown.

Leaves:
- *Size.*—Medium. Average length — 4¼". Average width — 1⅝".
- *Form.*—Obovate; acutely pointed.
- *Thickness.*—Medium.
- *Texture.*—Smooth.
- *Margin.*—Serrate.
- *Petiole.*—Medium length. Medium thickness.
- *Glands.*—Average number 2. Positioned on base of blade, opposite, small, globose.
- *Color.*—Top side — deep green (28-E-7 to 28-E-8). Under side — bracken green (29-D-7 to 29-E-7).

Flower buds:
- *Size.*—Medium.
- *Length.*—Medium.
- *Form.*—Plump; free.

Flowers:
- *Blooming period.*—Date of first bloom — Feb. 25, 1977. Date of full bloom — Mar. 1, 1977. Early as compared to other varieties.
- *Color.*—White.

Fruit:
- *Maturity when described.*—Eating ripe.
- *Date of first picking.*—June 1, 1977.

*Date of lasting picking.*—June 8, 1977.

*Size.*—Medium. Average diameter axially 2". Average transversely in suture plane 2⅛".

*Form.*—Uniform. Symmetrical. Globose to slightly flattened on stem end.

*Suture.*—Shallow. Extends from base to apex.

*Ventral surface.*—Lips usually equal.

*Cavity.*—Rounded to slightly elongated in suture plane. Average depth — ¼". Average breadth — 7/16.

*Base.*—Retuse.

*Apex.*—Rounded to vary slight pistil point.

*Stem.*—Average length — ½". Average width — 3/32".

Skin:

*Thickness.*—Medium.

*Texture.*—Medium.

*Tendency to crack.*—None.

*Down.*—Wanting.

*Color.*—Red (9-C-8) to (10-D-8).

Flesh:

*Texture.*—Firm. Meaty.

*Ripens.*—Evenly.

*Flavor.*—Mild-subacid.

*Eating quality.*—Good.

*Color.*—From melon yellow (5-A-6) to cadmium orange (5-A-8).

Stone:

*Type.*—Clingstone — adheres to flesh over entire surface.

*Size.*—Average length — 1". Average width — 9/16". Average thickness — 5/16".

*Color.*—From brownish orange (7-C-6) to light brown (7-D-6).

*Base.*—Straight.

*Apex.*—Acuminate.

*Sides.*—Equal.

*Surface.*—Irregularly furrowed and ridged near base.

*Dorsal edge.*—Full with broad groove.

*Ventral edge.*—Thin.

*Tendency to split.*—None.

Use: Market.

Keeping quality: Very good.

Shipping quality: Very good.

The plum tree and its fruit herein described may vary in slight detail due to climatic and soil conditions under which the variety may be grown. The description is that of the variety produced under ecological conditions prevailing at Modesto, Calif. and the characteristics are found to hold true in asexual reproduction of the variety.

I claim:

1. A new and distinct variety of plum tree, as illustrated and described, which is a regular and productive bearer of medium to large, firm, clingstone fruit, having yellow flesh and a red skin color; characterized, in comparison to the Red Beaut, (U.S. Plant Pat. No. 2,539); by fruit which ripens 2 to 3 days earlier, is of slightly larger in size, is clingstone instead of freestone, has yellow flesh color instead of red flesh color.

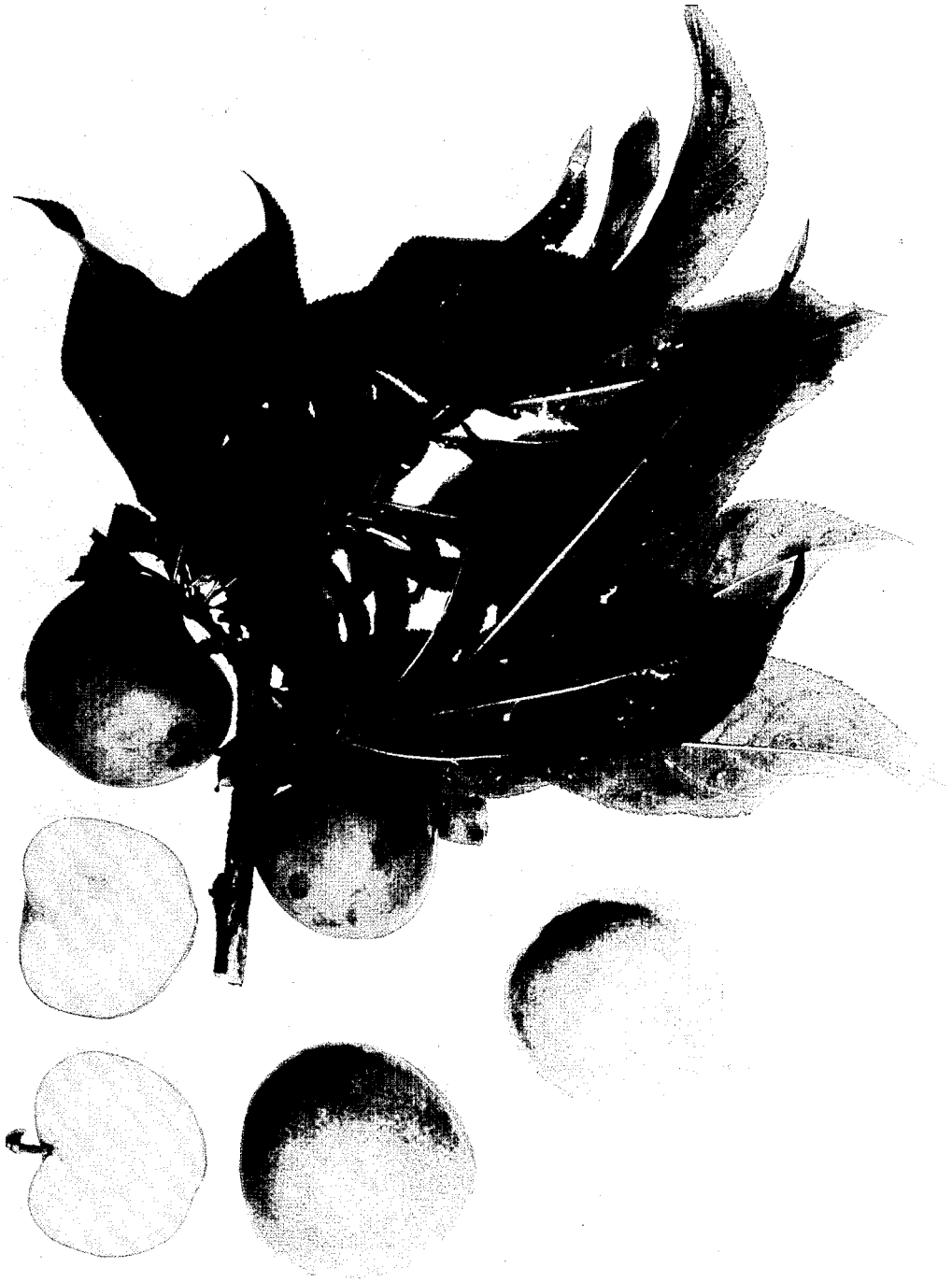

* * * * *